United States Patent [19]

Suzuki et al.

[11] Patent Number: 4,831,198
[45] Date of Patent: * May 16, 1989

[54] METHOD FOR ADSORPTIVE SEPARATION OF DICHLOROTOLUENES

[75] Inventors: Makoto Suzuki, Koriyama; Toshitaka Kaneshiki, Tokyo; Tadayoshi Haneda, Koriyama; Sueo Kanno, Koriyama; Yuichi Hane, Koriyama; Toshiyuki Endo, Koriyama; Yoshihiko Abe, Koriyama, all of Japan

[73] Assignee: Hodogaya Chemical Co., Ltd., Tokyo, Japan

[*] Notice: The portion of the term of this patent subsequent to Oct. 11, 2005 has been disclaimed.

[21] Appl. No.: 60,862

[22] Filed: Jun. 12, 1987

Related U.S. Application Data

[63] Continuation-in-part of Ser. No. 844,812, Mar. 27, 1986, abandoned, and a continuation-in-part of Ser. No. 62,385, Jun. 15, 1987.

[30] Foreign Application Priority Data

Apr. 15, 1985 [JP] Japan .................. 60-078445
Jun. 18, 1986 [JP] Japan .................. 61-140212
Jun. 23, 1986 [JP] Japan .................. 61-147051

[51] Int. Cl.⁴ .................................. C07C 17/38
[52] U.S. Cl. ........................................ 570/211
[58] Field of Search ........................... 570/211

[56] References Cited

U.S. PATENT DOCUMENTS 4,254,062  3/1981  Wambach ................. 570/211
4,453,029  6/1984  Dessau ..................... 570/211

FOREIGN PATENT DOCUMENTS 0199212  10/1986  European Pat. Off. ....... 570/211
2166734   5/1986  United Kingdom ........... 570/211

Primary Examiner—Werren B. Lone
Attorney, Agent, or Firm—Oblon, Fisher, Spivak, McClelland & Maier

[57] ABSTRACT

A method for selectively separating 2,6-dichlorotoluene from a mixture of dichlorotoluene isomers by means of a zeolite adsorber, characterized in that a zeolite selected from the group consisting of ZSM-5 zeolite, ZSM-8 zeolite, ZSM-11 zeolite, ZSM-21 zeolite, ZSM-35 zeolite, Zeta-1 zeolite, Zeta-3 zeolite and TPZ-3 zeolite, is used as the adsorber to selectively separate 2,6-dichlorotoluene as a non-adsorbed component.

11 Claims, 1 Drawing Sheet

METHOD FOR ADSORPTIVE SEPARATION OF DICHLOROTOLUENES

This application is continuation in part of U.S. patent application Ser. No. 844,612 filed Mar. 27, 1986 abandoned, and of Ser. No. 62,385, filed June 15, 1987, allowed.

BACKGROUND OF THE INVENTION

Field of the Invention

The present invention relates to a method for selectively separating 2,6-dichlorotoluene from a mixture of dichlorotoluene (hereinafter referred to simply as DCT) isomers by means of a zeolite adsorber.

DISCUSSION OF BACKGROUND 2,6-DCT is an important intermediate useful for the production of agricultural chemicals, medicines, dyestuffs, etc.

A mixture of DCT isomers is produced by chlorination of toluene or monochlorotoluene. The boiling points of the respective isomers are very close to one another, and it is very difficult to separate 2,6-DCT from the mixture by rectification. Therefore, as an industrial method, it is produced by dichlorination of p-toluene sulfonic acid, followed by desulfonation.

Further, U.S. Pat. No. 4,254,062 and Japanese Unexamined Patent Publication No. 199,642/1984 disclose a method for adsorptive separation of 2,6-DCT from a mixture of DCT isomers by means of faujasite type zeolite.

However, it is hardly possible to obtain 2,6-DCT of a high purity by the method for the production from p-toluene sulfonic acid. Further, this method is not economical. On the other hand, the latter method for the adsorptive separation by means of a zeolite is designed to separate and recover 2,6-DCT as an extract component from the mixture of DCT isomers. However, the adsorption of 2,6-DCT by faujasite type zeolite is not sufficient, and it is practically impossible to separate and recover 2,6-DCT in high purity. This method also has a drawback that 2,6-DCT can not be separated and recovered unless the adsorptive separation is conducted in the presence of a substituted benzene compound.

SUMMARY OF THE INVENTION

Under the circumstances, the present inventors have conducted extensive research for a method of effectively recovering by adsorptive separation 2,6-DCT in high purity from a mixture of DCT isomers. As a result, they have found specific catalysts which are capable of selectively separating 2,6-DCT as a non-adsorbed component. The present invention has been accomplished on the basis of this discovery.

The zeolites to be used in the present invention are well-known as isomerization catalysts. As an example for their application to adsorptive separation, an application to alkylbenzenes or phenols is known, but no application to the adsorptive separation of DCT isomers is known.

Namely, the present invention provides a method for selectively separating 2,6-dichlorotoluene from a mixture of dichlorotoluene isomers by means of a zeolite adsorber, characterized in that a zeolite selected from the group consisting of ZSM-5 zeolite, ZSM-8 zeolite, ZSM-11 zeolite, ZSM-21 zeolite, ZSM-35 zeolite, Zeta-1 zeolite, Zeta-3 zeolite and TPZ-3 zeolite, is used as the adsorber to selectively separate 2,6-dichlorotoluene as a non-adsorbed component.

BRIEF DESCRIPTION OF THE DRAWINGS

In the accompanying drawing.

DETAILED DESCRIPTION OF THE PREFERRED EMBODIMENTS

Figure 1:
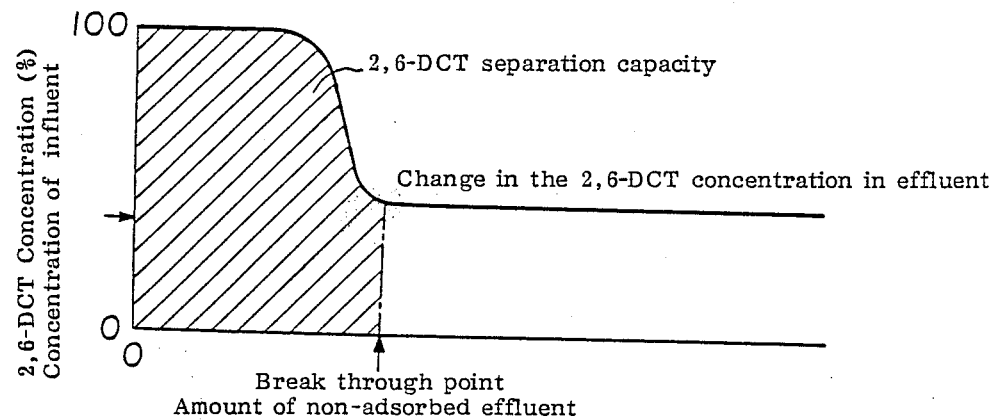
FIG. 1 is a break through curve of an adsober showing the amount of 2,6-DCT effluent till the break through point of the zeolite of the present invention when a mixture of DCT isomers was subjected to adsorptive separation by means of the zeolite.

The zeolite to be used in the present invention is an adsorber having an extremely peculiar characteristic such that it does not adsorb 1,2,3-tri-substituted benzenes including 2,6-DCT intended by the present invention as a representative component, while strongly adsorbing 1,2,4-tri-substituted benzenes.

Thus, it is possible to selectively and efficiently separate 2,6-DCT of a high purity by using the adsorber of the present invention.

The mixture of DCT isomers to be used in the present invention is a mixture of DCT isomers obtained by chlorination of toluene, which comprises 2,3-DCT (8-12% by weight), 2,4-DCT (20-35% by weight), 2,5-DCT (25-55% by weight), 2,6-DCT (5-25% by weight) and 3,4-DCT (5-12% by weight), or a mixture of DCT isomers obtained by chlorination of o-chlorotoluene which comprises 2,3-DCT (5-20% by weight), 2,4-DCT (10-25% by weight), 2,5-DCT (30-70% by weight) and 2,6-DCT (5-30% by weight).

The mixtures of DCT isomers obtained by such chlorinations may be used as they are. Preferably, however, they are firstly separated by rectification into distillation-separable fractions, and the fraction containing 2,6-DCT is subjected to the method of the present invention. Namely, they may be separated into a fraction having a boiling point of about 201° C. comprising 2,4-DCT, 2,5-DCT and 2,6-DCT, and a fraction having a boiling point of from about 208° to 209° C. comprising 2,3-DCT and/or 3,4-DCT, by rectification. The method of the present invention is effective particularly for the separation and recovery of 2,6-DCT from the former fraction of a mixture of DCT isomers.

The ZSM zeolites to be used in the present invention include ZSM-8 as disclosed in e.g. U.K. Pat. No. 1,334,243, ZSM-11 as disclosed in Japanese Examined Patent Publication No. 23,280/1978, ZSM-21 as disclosed in U.S. Pat. No. 4,001,346, ZSM-35 as disclosed in Japanese Unexamined Patent Publication No. 144,500/1978, zeolite Zeta-1 as disclosed in Japanese Unexamined Patent Publication No. 67299/1976 and zeolite Zeta-3 as disclosed in Japanese Unexamined Patent Publication No. 67,298/1976.

The ZSM-5 type zeolite to be used in the present invention is a high silica content zeolite represented by the following general formula and is a zeolite belonging to a Pentasil group. The crystal structure is a rhombic system belonging to a Pnma space group, wherein the lattice constants are a=20.1 Å, b=19.9 Å and c=13.4 Å.

$Na_nAl_nSi_{96-n}O_{192} \cdot mH_2O$ ($n<27$, $m \leq 16$)

The TPZ-3 zeolite to be used in the present invention is a high silica content zeolite represented by the following general formula:

$Na_2O \cdot Al_2O_3 \cdot xSiO_2$ ($x \geq 10$)

As expressed in the form of an anhydrous oxide. It shows an X-ray diffraction pattern which is entirely different from conventional ZSM zeolites such as ZSM-5, ZSM-11, ZSM-12 and ZSM-38 or from Zeta-3 zeolite, and its properties are also different therefrom.

In the above formulas, the sodium ions can easly be exchanged by other cations, as is well-known to those skilled in the art of zeolites.

As the cation component of the zeolites to be used in the present invention, any component may basically be used. However, it is preferably at least one cation selected from the group consisting of monovalent and divalent metals, protons and ammonium ions. Particularly preferred are protons.

The ion exchange of these cations may be conducted preferably by contacting to zeolites an aqueous solution of a nitrate of one or more cations to be exchanged with the cations of the zeolites, as an ion exchange treating solution. It is also preferred to employ an aqueous solution of other soluble salts such as chlorides instead of nitrates. Further, such cations may be treated only once by a single ion exchange treatment with the ion exchange solution, or may be treated several times. The treating system may be a batch system or a continuous system. The temperature for the treatment is usually within a range of from 20° to 100° C., and to facilitate the exchange rate, the temperature is preferably from 50° to 100° C. After the ion exchange treatment, it is necessary to conduct washing with water adequately so that e.g. $NO_3^-$ or $Cl^-$ ions are no longer detected.

Prior to the use of the zeolite as a catalyst, it is necessary to remove water of crystallization therefrom. Usually, the content of water of crystallization can be substantially reduced at a temperature of 100° C. or higher. Preferably, the zeolite is heated at a temperature of from 300° to 600° C., whereby almost all water of crystallization can be removed.

The zeolite to be used in the present invention may be in the form of a powder, or crushed blocks, or may be shaped products obtained by e.g. compression molding and extrusion molding. Further if necessary, a binder such as alumina sol or clay may be added at the time of the molding. In a small scale operation, the xeolite may be used in a powder form. For an industrial operation, it is preferred to employ a molded product in the form of pellets having a diameter of from 0.1 to 10 mm to avoid a pressure loss. The shape of the zeolite may be suitably selected depending upon the particular apparatus.

The $SiO_2/Al_2O_3$ ratio is not particularly restricted, and is preferably within a range of from 10 to 200.

A method for the production of ZSM-5 and its composition are disclosed in Japanese Examined Patent Publication No. 10064/1971, and its crystal structure is described in detail in "Nature" vol 271, No. 30, March issue, p 437 (1978). Namely, ZSM-5 is prepared by using an organic amine, and has characteristic pores with a ten-membered ring of oxygen.

A method for the production of TPZ-3 and its composition are disclosed in Japanese Unexamined Patent Publication No. 95821/1982. Namely, TPZ-3 is prepared by using N,N,N,N',N',N' -hexaalkyl-1,6-hexanediammonium ions, and has characteristic pores larger than ZSM-5. For the operation of the method of the present invention a batch method using a conventional fixed bed system or a continuous method may be used for the separation step.

The separation step of the present invention may be carried out basically by a cycle of adsorption, washing, desorption and regeneration of the adsober, with one or more adsorption chambers packed with the adsorber.

Namely, a mixture of DCT isomers including 2,6-DCT as the desired substance and at least one other DCT isomer except for 2,3-DCT, is contacted in an adsorption chamber with the adsober of the present invention, whereby the desired 2,6-DCT can selectively be separated as a non-adsorbed component while having other components strongly adsorbed on the adsorber.

The adsorption of the present invention may be conducted within a temperature range of from room temperature to about 300° C., preferably from 150° to 250° C. If the temperature is higher than 300° C., a side reaction such as a disproportionation reaction of DCT is likely to take place, such being undesirable.

The reaction pressure is usually with in a range of from atmospheric pressure to about 50 kg/cm², preferably from atmospheric pressure to about 30 kg/cm². If the pressure is higher than about 50 kg/cm², the operation will be costly, such being undesirable. At the time of adsorption, a substance which does not affect the adsorption-desorption, may be added to the mixture of DCT isomers, as a diluting solvent.

There is no particular restriction as to the manner of desorbing DCT isomers strongly adsorbed by the adsorptive separation of the present invention. There may be employed various methods such as (1) desorption by a temperature difference, (2) desorption by a pressure difference, (3) desorption by an inert gas, (4) desorption by steam or (5) desorption by substitution by a third component, or a combination of these method. Among them, desorption by steam is preferred.

With respect to the ability of the zeolite to be used in the method of the present invention for the adsorptive separation of the mixture of DCT, for instance, in a case where a mixture comprising 2,4-DCT, 2,5-DCT and 2,6-DCT is subjected to adsorptive separation with ZSM-5, 2,4-DCT and 2,5-DCT are adsorbed, while desired 2,6-DCT will be separated without being adsorbed. Namely, ZSM-5 has an extremely large adsorption capacity for 2,4-DCT AND 2,5-DCT, and the concentration of 2,6-DCT in the non-adsorbed effluent changes idealy as shown by the break through curve of FIG. 1. Thus, the capability of ZSM-5 for adsorptive separation can be represented by the amount of 2,6-DCT effluent (% by weight as pure product) up to the break through point per 1 g of zeolite.

2,6-DCT separation capacity (wt %)=A(g)×B(wt %)/ZSM-5 (g)

A: Total amount (g) of the effluent up to the break through point

B: Average 2,6-DCT concentration (wt %) in the effluent

The higher the 2,6-DCT separation capacity, the more advantageous for the industrial operation, and consequently, it is possible to obtain 2,6-DCT of a high purity efficiently.

Thus, according to the method of the present invention, it is possible not only to selectively obtain 2,6-DCT of a high purity which used to be difficult to accomplish by the adsorptive separation of a mixture of DCT isomers by means of the zeolite, but also to treat other DCT isomers separated as strongly adsorbed components, for isomerization to be used again for adsorptive separation, whereby respective isomers can effectively be utilized. Further, the zeolites of the present invention can be reused for a long period of time. Thus, the contribution of the present invention to the industrial application is extremely high.

Now, the present invention will be described in further detail with reference to Examples. However, it should be understood that the present invention is by no means restricted to such specific Examples.

Reference Example 1

A powder of ZSM-5 type zeolite comprising 90.1% by weight of $SiO_2$, 6.1% by weight of $Al_2O_3$ and 3.8% by weight of $Na_2O$ with a $SiO_2/Al_2O_3$ ratio of 25.1, was prepared in accordance with the process of Example 1 Japanese Examined Patent Publication No. 10064/1971. Then, the zeolite powder was subjected to ion exchange treatment five times by using an aqueous solution containing 10% by weight of ammonium nitrate (solid-liquid ratio: 2.0 liter/kg, 95° C.), thoroughly washed with water, dried at 150° C. for 5 hours, and then calcined at 500° C. for 3 hours to obtain a H-ZSM-5 type zeolite powder. From the X-ray analysis, this H-ZSM-5 type zeolite, was found to be the same as the H-ZSM-5 manufactured by Mobil Oil Corp.

Reference Example 2

In the same manner as in Reference Example 1, a ZSM-5 type zeolite powder comprising 93.6% by weight of $SiO_2$, 3.2% by weight of $Al_2O_3$ and 3.2% by weight of $Na_2O$ with a $SiO_2/Al_2O_3$ ratio of 49.6, was obtained. This zeolite powder was treated in the same manner as in Reference Example 1 to obtain a H-ZSM-5 type zeolite powder Example 1

8.43 g of the H-ZSM-5 type zeolite powder of Reference Example 1 was packed in a metal column having an inner diameter of 9.8 mm and a length of 16.3 cm, and a mixture of DCT isomers was introduced at a rate of 0.1 ml/min under a nitrogen pressure of 2 kg/cm² at 200° C. The mixture of DCT isomers introduced, had a composition of 2,4-DCT/2,5-DCT/2,6-DCT=24/44/32 by weight ratio.

The composition of the non-adsorbed effluent from the outlet of the column, was analyzed by gas chromatograpy, whereby it was found that the initial concentration of 2,6-DCT was 100%, and the 2,6-DCT concentration gradually decreased and upon expiration of 10 minutes, reached the break through point where the composition of the non-adsorbed effluent was the same as the feed liquid.

The total amount of the non-adsorbed effluent up to the break through point was 0.71 g.

The average DCT composition of the total effluent was 2,4-DCT/2,5-DCT/2,6-DCT=7.1/13.4/79.5 by weight ratio.

Thus, the 2,6-DCT separation capacity was 6.70% by weight.

Examples 2 to 5

The adsorption operation was conducted in the same manner by using the same apparatus as in Example 1 except that the cation of H-ZSM-5 type zeolite of Reference Example 1 was changed to calcium, magnesium, copper and sodium, respectively, whereby the 2,6-DCT separation capacity was measured. The results are shown in the following Table.

| Example No. | Type of cation | 2,6-DCT separation capacity (wt %) |
| --- | --- | --- |
| 2 | Ca | 5.21 |
| 3 | Mg | 2.73 |
| 4 | Cu | 4.82 |
| 5 | Na | 4.67 |

The cation exchange was conducted by treating the H-ZSM-5 type zeolite with an aqueous solution containing from 5 to 10% by weight of a nitrate in the same manner as in Reference Example 1.

Examples 6 and 7

The adsorption operation was conducted in the same manner by using the same apparatus as in Example 1 except that the temperature for adsorption was changed, whereby the 2,6-DCT separation capacity was measured. The results are shown in the following Table. In the case where the temperature for adsorption was 300° C., a disproportionation reaction took place, and the production of o-chlorotoluene and toluene as by-products was observed.

| Ex. No. | Adsorption temperature (°C.) | Composition of total effluent up to the break trough point | | | | | 2,6-DCT separation capacity (wt %) |
| --- | --- | --- | --- | --- | --- | --- | --- |
| | | 2,4-DCT | 2,5-DCT | 2,6-DCT | o-chlorotoluene | Toluene | |
| 6 | 250 | 7.4 | 13.5 | 79.1 | 0 | 0 | 6.47 |
| 7 | 300 | 7.1 | 12.9 | 75.6 | 4.2 | 0.1 | 6.10 |

Examples 8 to 10

The adsorption operation was conducted in the same manner by using the same apparatus as in Example 1 except that the feed liquid mixture of DCT isomers was changed. The composition of the feed liquid and the average composition of the non-adsorbed effluent up to the break through point are shown in the following Table.

| Ex. No. | Influent composition (wt %) | | | | | Effluent composition (wt %) | | | | |
| --- | --- | --- | --- | --- | --- | --- | --- | --- | --- | --- |
| | 2,3-DCT | 2,4-DCT | 2,5-DCT | 2,6-DCT | 3,4-DCT | 2,3-DCT | 2,4-DCT | 2,5-DCT | 2,6-DCT | 3,4-DCT |
| 8 | — | 40.2 | 36.4 | 23.4 | — | — | 8.5 | 12.9 | 78.6 | — |
| 9 | 14.7 | 22.8 | 32.9 | 29.6 | — | 28.1 | 7.6 | 13.5 | 50.8 | — |
| 10 | 20.1 | 14.5 | 25.4 | 20.4 | 19.6 | 33.5 | 6.4 | 11.1 | 43.1 | 5.9 |

Example 11

The same operation as in Example 1 was conducted except that 7.85 g of the H-ZSM-5 type zeolite of Reference Example 2 was employed. The following results were obtained.

The total amount of the non-adsorbed effluent up to the break through point: 0.7 g The average DCT composition of this total effluent was 2,4-DCT/2,5-DCT/2,6-DCT=9.9/20.4/69.7 by weight ratio Thus, the 2,6-DCT separation capacity was 6.22% by weight.

Example 12

The same operation as in Example 1 was conducted except that 11.24 g of silicalite (JE-15, manufactured by Union Showa K.K.) which is regarded as SZM-5 type zeolite containing no substantial aluminum component. The following results were obtained.

The total amount of the non-adsorbed effluent up to the break through point: 1.75 g The average DCT composition of this total effluent was 2,4-DCT/2,5-DCT/2,6-DCT=18.5/35.5/46.0 by weight ratio Thus, the 2,6-DCT separation capacity was 7.16% by weight.

Reference Example 3

ZSM-11 zeolite powder having a molar ratio of $SiO_2/Al_2O_3 = 50.8$ was obtained in accordance with the method of Example 1 of Japanese Examined Patent Publication No. 23280/1978. Then, the powder was subjected to ion exchange five times with a 10 wt % ammonium nitrate aqueous solution (liquid-solid ratio of 2.0 l/kg, 95° C.), then thoroughly washed with water, dried at 150° C. for 5 hours, and thereafter sintered at 500° C. for 3 hours to obtain acid type H-ZSM-11 zeolite powder. The results of the X-ray analysis of this H-ZSM-11 zeolite agreed to those of H-ZSM-11 made by Mobile Company.

Reference Example 4

ZSM-8 zeolite powder was prepared in accordance with the method of the Examples of U.K. Pat. No. 1,334,243.

This powder was treated in the same manner as in Reference Example 3 to obtain H-ZSM-8 zeolite powder.

Reference Example 5

ZSM-21 zeolite powder was prepared in accordance with the method of the Examples of U.S. Pat. No. 4,001,346.

This powder was treated in the same manner as in Reference Example 3 to obtain H-ZSM-21 zeolite powder.

Reference Example 6

ZSM-35 zeolite powder was prepared in accordance with the method of the Examples of Japanese Unexamined Patent Publication No. 144,500/1978.

The powder was treated in the same manner as in Reference Example 3 to obtain H-ZSM-35 zeolite powder.

Reference Example 7

Zeta-1 zeolite powder was prepared in accordance with the method of the Examples of Japanese Unexamined Patent Publication No. 67,299/1976.

The powder was treated in the same manner as in Reference Example 3 to obtain H-Zeta-1 zeolite powder.

Reference Example 8

Zeta-3 zeolite powder was prepared in accordance with the method of the Examples of Japanese Unexamined Patent Publication No. 67,298/1976.

The powder was treated in the same manner as in Reference Example 3 to obtain H-Zeta-3 zeolite powder.

Example 13

8.48 g of H-ZSM-11 zeolite powder of Reference Example 3 was packed to a metal column having an internal diameter of 9.8 mm and a length of 16.3 cm, and a mixture of DCT isomers was introduced at a rate of 0.1 ml/min. at 200° C. under a nitrogen pressure of 2 kg/cm$^2$. The composition of the mixture of DCT isomers introduced was as follows:

2,4-/2,5-/2,6-DCT=24.1/43.7/32.2 by weight ratio

The composition of the non-adsorbed effluent from the outlet of the column was analyzed by gas chromatography, whereby it was found that the initial 2,6-DCT concentration was 100%, the 2,6-DCT concentration gradually decreased, and upon expiration of 10 minutes, the composition of the non-adsorbed effluent became the same as the composition of the influent, thus reached the break through point. The total amount of the non-adsorbed effluent up to the break through point was 0.70 g. The average composition of the total effluent was as follows:

2,4-/2,5-/2,6-DCT=7.2/13.6/79.2 by weight ratio

Thus, the 2,6-DCT separation capacity was 6.54% by weight.

Comparative Examples 1 to 4

The adsorption operation was repeated by using the same apparatus, method and DCT isomer mixture as used in Example 1 by changing the type of the zeolite. The zeolites used were Na-X zeolite (Molecular Sieve 13X, manufactured by Union Showa K.K.), K-Y zeolite (TSZ-320 KOA, manufactured by Toyo Soda Manufacturing Company Limited), Na-A zeolite (Molecular Sieve 4A, manufactured by Union Showa K.K.), and K-L zeolite (TSZ-500 KOA, manufactured by Toyo Soda Manufacturing Company Limited). 10 g of such zeolite was packed in a metal column. The average composition of DCT in the non-adsorbed effluent up to the break through point is shown in the following Table.

| Comparative Examples | Type of Zeolite | Effluent Composition (wt %) | | | Amount (g) |
|---|---|---|---|---|---|
| | | 2,4-DCT | 2,5-DCT | 2,6-DCT | |
| Comparative Example 1 | Na—X | 30.9 | 43.5 | 25.6 | 1.4 |
| Comparative Example 2 | K—Y | 13.4 | 37.3 | 49.3 | 1.4 |
| Comparative Example 3 | Na—A | 24.0 | 44.0 | 32.0 | No adsorptive separation |
| Comparative Example 4 | K—L | 24.0 | 44.0 | 32.0 | No adsorptive separation |

Examples 14 to 17

The adsorption operation was conducted by using the same apparatus and method as used in Example 13 except that the cations of H-ZSM-11 zeolite of Reference Example 3 were changed to calcium, magnesium, copper and sodium, respectively. The 2,6-DCT separation capacity was measured. The results are shown in the following Table.

| Example No. | Type of cations | 2,6-DCT separation capacity (wt %) |
|---|---|---|
| 14 | Ca | 4.95 |
| 15 | Mg | 2.66 |
| 16 | Cu | 4.61 |
| 17 | Na | 4.69 |

The exchange of cations were conducted by treating H-ZSM-11 zeolite with a 5-10 wt % nitrate aqueous solution in the same manner as in Reference Example 3.

Examples 18 and 19

The operation was conducted by using the same apparatus and method as used in Example 13 by changing the temperature for adsorption. The 2,6-DCT separation capacity was measured. The results are shown in the following Table. However, when the adsorption temperature was 300° C., a disproportionation reaction occured, whereby o-chlorotoluene and toluene were produced as by-products.

| Ex. No. | Adsorption temperature (°C.) | Composition of the total effluent up to the break through point | | | | | 2,6-DCT separation capacity (wt %) |
|---|---|---|---|---|---|---|---|
| | | 2,4-DCT | 2,5-DCT | 2,6-DCT | o-chloro-toluene | toluene | |
| 18 | 250 | 7.4 | 13.6 | 79.0 | 0 | 0 | 6.46 |
| 19 | 300 | 7.2 | 13.5 | 75.0 | 3.9 | 0.1 | 5.96 |

Examples 20 to 22

The adsorption operation was conducted by using the same apparatus and method as used in Example 13 by changing the proportions of the mixture of DCT isomers introduced. The composition of the influent and the average composition of the non-adsorbed effluent up to the break through point are shown in the following Table.

| Ex. No. | Influent composition (wt %) | | | | | Effluent composition (wt %) | | | | |
|---|---|---|---|---|---|---|---|---|---|---|
| | 2,3-DCT | 2,4-DCT | 2,5-DCT | 2,6-DCT | 3,4-DCT | 2,3-DCT | 2,4-DCT | 2,5-DCT | 2,6-DCT | 3,4-DCT |
| 20 | — | 40.2 | 36.4 | 23.4 | — | — | 12.1 | 11.7 | 76.2 | — |
| 21 | 14.7 | 22.8 | 32.9 | 29.6 | — | 26.9 | 9.0 | 13.3 | 50.8 | — |
| 22 | 20.1 | 14.5 | 25.4 | 20.4 | 19.6 | 36.1 | 5.4 | 9.8 | 41.4 | 7.3 |

Examples 23 to 27

The adsorption operation was conducted by using the same apparatus and method and DCT isomer mixture as used in Example 13 except that H-ZSM-11 zeolite used in Example 13 was changed to ZSM type zeolite powder prepared in Reference Examples 4 to 8. The 2,6-DCT separation capacity was measured. The results are shown in the following Table.

| Ex. No. | Type of ZSM zeolite | | Effluent composition (wt %) | | | Separating capacity (wt %) |
|---|---|---|---|---|---|---|
| | Name | Reference Example No | 2,4-DCT | 2,5-DCT | 2,6-DCT | |
| 23 | H-ZSM-8 | 4 | 10.8 | 19.8 | 69.4 | 5.48 |
| 24 | H-ZSM-21 | 5 | 10.3 | 18.9 | 70.8 | 5.65 |
| 25 | H-ZSM-35 | 6 | 8.8 | 16.3 | 74.9 | 5.96 |
| 26 | H-Zeta-1 | 7 | 7.5 | 13.7 | 78.8 | 6.37 |
| 27 | H-Zeta-3 | 8 | 11.3 | 21.1 | 67.6 | 5.42 |

Reference Example 9

TPZ-3 zeolite powder having a molar ratio of SiO$_2$/Al$_2$O$_3$=100 was prepared in accordance with the method of Example 1 of Japanese Unexamined Patent Publication No. 95821/1982.

Then, the powder was treated in the same manner as in Reference Example 3, to obtain acid type H-TPZ-3 zeolite powder. The results of the X-ray analysis of this H-TPZ-3 zeolite agreed to those of H-TPZ-3 manufactured by Teijin Yuka K.K.

Reference Example 10

TPZ-3 zeolite powder having a molar ratio of SiO$_2$/Al$_2$O$_3$=120 was prepared in the same manner as in Reference Example 9.

The powder was treated in the same manner as in Reference Example 3 to obtain H-TPZ-3 zeolite powder.

Examples 28 to 31

8.43 g of H-TPZ-3 zeolite powder of Reference Example 9 was packed in a metal column having an internal diameter of 9.8 mm and a length of 16.3 cm, and a mixture of DCT isomers was introduced at a rate of 0.1 mm/min. at 200° C. under a nitrogen pressure of 2 kg/cm$^2$. The composition of the mixture of DCT isomers introduced was as follows:

2,4-/2,5-/2,6-DCT=24.1/43.7/32.2 by weight ratio

The composition of the non-adsorbed effluent from the outlet of the column was analyzed by gas chromatography, whereby it was found that the initial 2,6-DCT concentration was 100%, and the 2,6-DCT concentration gradually decreased, and upon expiration of 10 minutes, the composition of the non-adsorbed effluent became the same as the composition of the influent, and thus reached the break through point.

The total amount of the non-adsorbed effluent up to the break through point was 0.70 g.

The average composition of DCT in the total effluent was as follows:

2,4-/2,5-/2,6-DCT=7.5/14.0/78.5 by weight ratio

Thus, the 2,6-DCT separation capacity was 6.52% by weight. Then, nitrogen gas was introduced at the same temperature under a pressure of 3 kg/cm$^2$ for 30 minutes, to discharge and wash the deposited mixture of DCT isomers. The discharged amount was 1.2 g.

Then, a gas mixture of steam (molar ratio: 0.33) and nitrogen (molar ratio: 0.67) was introduced at a rate of 60 mm/min. at the same temperature under a pressure of 6 kg/cm². The adsorbed 2,4-DCT and 2,5-DCT were desorbed and discharged together with water, and upon expiration of about 30 minutes, the discharge of DCT was completed. The total amount of the desorbed DCT effluent was 0.28, and the average composition of the total effluent was as follows:

2,4-/2,5-/2,6-DCT=31.4/57.8/10.8 by weight ratio

Further, a nitrogen gas was introduced at a rate of 40 ml/min. at the same temperature under a pressure of 6 kg/cm² for 2 hours to dry and regenerate the adsorber.

After the completion of the regeneration, a total of 4 cycles including Example 16 were repeated, with one cycle comprising the above adsorption-washing-desorption-regeneration steps. The results are shown in the following Table. The crystallinity of the zeolite after the repetition of the 4 cycles was analyzed by the X-ray analysis, and no destruction the crystal structure was observed.

Effluent composition

| Ex. No. | Cycle | during the adsorption step (wt %) | | | Total effluent during the adsorption step (g) | Separaton capacity (wt %) |
|---|---|---|---|---|---|---|
| | | 2,4-DCT | 2,5-DCT | 2,6-DCT | | |
| 29 | 2nd | 8.9 | 16.4 | 74.7 | 0.65 | 5.76 |
| 30 | 3rd | 8.7 | 16.2 | 75.1 | 0.64 | 5.70 |
| 31 | 4th | 8.9 | 16.4 | 74.4 | 0.66 | 5.85 |

Examples 32 to 35

The adsorption operation was conducted by using the same apparatus and method as used in Example 28 except that the cations of H-TPZ-3 zeolite of Reference Example 9 were changed to calcium, magnesium, copper and sodium, respectively. The 2,6-DCT separation capacity was measured. The results are shown in the following Table.

| Example No. | Type of cations | 2,6-DCT separation capacity (wt %) |
|---|---|---|
| 32 | Ca | 5.20 |
| 33 | Mg | 2.65 |
| 34 | Cu | 4.79 |
| 35 | Na | 4.69 |

The cation exchange was conducted by treating H-TPZ-3 zeolite with a 5-10 wt % nitrate aqueous solution in the same manner as in Reference Example 1.

Examples 36 and 37

The operation was conducted by using the same apparatus and method as used in Example 28 by changing the temperature for adsorption. The 2,6-DCT separation capacity was measured. The results are shown in the following Table. However, when the adsorption temperature was 300° C., a disproportionation reaction took place, whereby o-chlorotoluene and toluene were produced as by-products.

| Ex. No. | Adsorption temperature (°C.) | Composition of the total effluent up to the break through point | | | | | 2,6-DCT separation capacity (wt %) |
|---|---|---|---|---|---|---|---|
| | | 2,4-DCT | 2,5-DCT | 2,6-DCT | o-chlorotoluene | toluene | |
| 36 | 250 | 7.7 | 14.2 | 78.1 | 0 | 0 | 6.46 |
| 37 | 300 | 7.4 | 13.5 | 74.9 | 4.1 | 0.1 | 6.08 |

Examples 38 to 40

The adsorption operation was conducted by using the same apparatus and method as used in Example 28 by changing the proportions of the mixture of DCT isomers introduced. The composition of the influent and the average composition of the non-adsorbed effluent up to the break through point are shown in the following Table.

| Ex. No. | Influent composition (wt %) | | | | | Effluent composition (wt %) | | | | |
|---|---|---|---|---|---|---|---|---|---|---|
| | 2,3-DCT | 2,4-DCT | 2,5-DCT | 2,6-DCT | 3,4-DCT | 2,3-DCT | 2,4-DCT | 2,5-DCT | 2,6-DCT | 3,4-DCT |
| 38 | — | 40.2 | 36.4 | 23.4 | — | — | 12.1 | 11.5 | 76.4 | — |
| 39 | 14.7 | 22.8 | 32.9 | 29.6 | — | 26.2 | 9.3 | 14.1 | 50.4 | — |
| 40 | 20.1 | 14.5 | 25.4 | 20.4 | 19.6 | 30.9 | 6.8 | 11.9 | 42.5 | 7.9 |

Example 41

The operation was conducted in the same manner as in Example 28 except that 8.19 g of H-TPZ-3 zeolite powder of Reference Example 10 was used. The following results were obtained.

Total amount of non-adsorbed effluent up to the break through point: 0.69 g.

The average composition of DCT in this total effluent was as follows:

2,4-/2,5-/2,6-DCT=7.4/14.0/78.6 by weight ratio

Thus, the 2,6-DCT separation capacity was 6.62% by weight.

What is claimed is:

1. A method for selectively separating 2,6-dichlorotoluene from a mixture of 2,6-dichlorotoluene and at least one dichlorotoluene isomer selected from the group consisting of 2,3-, 2,4-, 2,5-, and 3,4-dichlorotoluenes by means of a zeolite adsorber selected from the group consisting of ZSM-5 zeolite, ZSM-8 zeolite, ZSM-11 zeolite, ZSM-21 zeolite, ZSM-35 zeolite, Zeta-1 zeolite, Zeta-3 zeolite and TPZ-3 zeolite, which comprises drying the zeolite adsorber, and contacting the mixture with the dried zeolite adsorber to selectively separate 2,6-dichlorotoluene as a non-adsorbed component.

2. The method according to claim 1, wherein said mixture is a mixture of 2,4-, 2,5- and 2,6-dichlorotoluenes.

3. The method according to claim 1, wherein the zeolite has cations selected from monovalent and divalent metals, protons and ammonium ions.

4. The method according to claim 1, wherein the zeolite is ZSM-5 zeolite having the formula:

$Na_nAl_nSi_{96-n}O_{192} \cdot mH_2O$ ($n<27$, $m \leq 16$).

5. The method according to claim 1, wherein the zeolite is TPZ-3 zeolite having the formula:

$$Na_2O \cdot Al_2O_3 \cdot xSiO_2 (x \geq 10)$$

as expressed in the form of an anhydrous oxide.

6. The method according to claim 1, wherein the zeolite contains no substantial water of crystallization.

7. The method according to claim 1, wherein the zeolite is in the form of pellets having an average diameter of from 0.1 to 10 mm.

8. The method according to claim 1, wherein the $SiO_2/Al_2O_3$ ratio in the zeolite is from 10 to 200.

9. The method according to claim 1, wherein the adsorption is conducted at a temperature of from room temperature to about 300° C.

10. The method according to claim 1, wherein the adsorption is conducted at a pressure of from atmospheric pressure to about 50 $kg/cm^2$.

11. The method according to claim 1, wherein desorption of the adsorbed dichlorotoluene isomers is accomplished with steam.

* * * * *